(12) United States Patent
Bentsen et al.

(10) Patent No.: US 6,375,871 B1
(45) Date of Patent: *Apr. 23, 2002

(54) METHODS OF MANUFACTURING MICROFLUIDIC ARTICLES

(75) Inventors: James G. Bentsen, North St. Paul; Raymond P. Johnston, Lake Elmo; Rolf W. Biernath, Maplewood; Richard J. Poirier, White Bear Lake, all of MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/099,562

(22) Filed: Jun. 18, 1998

(51) Int. Cl.[7] .............................. B29D 11/00; B29D 9/00
(52) U.S. Cl. ........................ 264/1.6; 156/242; 264/1.7; 422/100
(58) Field of Search .............................. 264/1.1, 1.36, 264/1.38, 1.7, 2.7, 1.6; 156/242, 244.11; 422/99, 100; 436/180; 204/600

(56) References Cited

U.S. PATENT DOCUMENTS

| | | |
|---|---|---|
| 3,511,381 A | 5/1970 | Alwall et al. |
| 3,520,300 A | 7/1970 | Flower, Jr. ................. 128/276 |
| 3,715,192 A | 2/1973 | Wenz et al. |
| 3,812,972 A | 5/1974 | Rosenblum |
| 3,993,566 A | 11/1976 | Goldberg et al. ...... 210/433 M |

(List continued on next page.)

FOREIGN PATENT DOCUMENTS

| | | |
|---|---|---|
| DE | 32 12 295 A1 | 10/1983 |
| DE | 42 10 072 A1 | 3/1993 |
| DE | 195 01 017 A1 | 7/1996 |
| EP | 0 039 291 A1 | 11/1981 |
| EP | 0 329 340 A2 | 8/1989 |

(List continued on next page.)

OTHER PUBLICATIONS

Article: "Fabrication of Novel Three–Dimensional Microstructures by the Anisotropic Etching of (100) and (110) Silicon", Ernest Bassous, *IEEE Transactions on Electron Devices,* vol. ED–25, No. 10, Oct. 1978.

Article: "Microtechnology Opens Doors to the Universe of Small Space", Peter Zuska *Medical Device & Diagnostic Industry,* Jan. 1997.

Article: "Processing of Three–Dimensional Microstructures Using Macroporous n–Type Silicon" Ottow et al. *J. Electrochem. Soc.,* vol. 143, No. 1, Jan. 1996.

Paper Submitted at Conference: L. J. Guérin et al., "Simple and Low Cost Fabrication of Embedded Microchannels by Using a New Thick–Film Photoplastic," 1997 International Conference on Solid–State Sensors and Actuators, *Digest of Technical Papers,* vol. 2, Sessions 3A1–4D3, Papers 3A1.01–4D3.14P, Jun. 16–19, 1997, Chicago, Illinois, USA, pp. 1419–1422.

Article: Becker et al., "Fabrication of Microstructures with High Aspect Ratios and Great Structural Heights by Synchrotron Radiation Lithography, Galvanoforming, and Plastic Moulding (LIGA Process)," *Microelectronic Engineering 4,* 1986, pp. 35–56.

(List continued on next page.)

*Primary Examiner*—Mathieu D. Vargot
(74) *Attorney, Agent, or Firm*—Christopher D. Gram; Paul W. Busse; James A. Rogers

(57) ABSTRACT

A process for preparing a molded article that includes: (a) bringing a moldable material and an open molding tool comprising a molding surface into line contact with each other to imprint a microfluid processing architecture pattern onto the moldable material and thereby form a molded article; and (b) separating the molded article from said molding surface. The invention also features various microfluid processing architecture-bearing, polymeric articles.

19 Claims, 13 Drawing Sheets

U.S. PATENT DOCUMENTS

| | | |
|---|---|---|
| 4,233,029 A | 11/1980 | Columbus ................ 23/230 R |
| 4,271,119 A | 6/1981 | Columbus |
| 4,277,966 A | 7/1981 | Rambauske |
| 4,392,362 A | 7/1983 | Little ........................ 62/514 R |
| 4,413,407 A | 11/1983 | Columbus .................... 29/825 |
| 4,533,352 A | 8/1985 | Van Beek et al. .......... 604/317 |
| 4,579,555 A | 4/1986 | Russo ........................ 604/282 |
| 4,601,861 A | 7/1986 | Pricone et al. .............. 264/1.6 |
| 4,639,748 A | 1/1987 | Drake et al. ............ 346/140 R |
| 4,668,558 A | 5/1987 | Barber |
| 4,677,705 A | 7/1987 | Schuster ..................... 15/398 |
| 4,758,481 A | 7/1988 | Fauvel |
| 4,867,876 A | 9/1989 | Kopf |
| 4,896,930 A | 1/1990 | Tsuchitani et al. ....... 350/96.12 |
| 4,906,439 A | 3/1990 | Grenner ...................... 422/56 |
| 4,913,858 A | 4/1990 | Miekka et al. .............. 264/1.3 |
| 4,950,549 A | 8/1990 | Rolando et al. |
| 5,014,389 A | 5/1991 | Ogilvie et al. ................ 15/353 |
| 5,061,029 A | 10/1991 | Ishikawa .................... 385/132 |
| 5,069,403 A | 12/1991 | Marentic et al. |
| 5,078,925 A | 1/1992 | Rolando et al. |
| 5,126,022 A | 6/1992 | Soane et al. ............ 204/180.1 |
| 5,133,516 A | 7/1992 | Marentic et al. |
| 5,136,678 A | 8/1992 | Yoshimura .................. 385/132 |
| 5,152,060 A | 10/1992 | Schubert et al. ....... 29/890.039 |
| 5,158,557 A | 10/1992 | Noreen et al. |
| 5,175,030 A | 12/1992 | Lu et al. ........................ 428/30 |
| 5,176,667 A | 1/1993 | DeBring .................... 604/356 |
| 5,200,248 A | 4/1993 | Thompson et al. |
| 5,227,008 A | 7/1993 | Klun et al. ................. 156/630 |
| 5,249,359 A | 10/1993 | Schubert et al. |
| 5,265,184 A | 11/1993 | Lebby et al. ............... 385/145 |
| 5,296,375 A | 3/1994 | Kricka et al. ............... 435/291 |
| 5,304,487 A | 4/1994 | Wilding et al. ............. 435/291 |
| 5,376,252 A | 12/1994 | Ekström et al. ......... 204/299 R |
| 5,399,486 A | 3/1995 | Cathey et al. |
| 5,411,858 A | 5/1995 | McGeehan et al. ............ 435/4 |
| 5,429,807 A | 7/1995 | Matson et al. .............. 422/131 |
| 5,437,651 A | 8/1995 | Todd et al. .................. 604/313 |
| 5,440,332 A | 8/1995 | Good |
| 5,445,934 A | 8/1995 | Fodor et al. .................... 435/6 |
| 5,450,235 A | 9/1995 | Smith et al. ................. 359/529 |
| 5,457,848 A | 10/1995 | Miwa ........................... 15/346 |
| 5,474,796 A | 12/1995 | Brennan .................... 427/2.13 |
| 5,498,392 A | 3/1996 | Wilding et al. ............. 422/68.1 |
| 5,500,071 A | 3/1996 | Kaltenbach et al. ..... 156/272.8 |
| 5,514,120 A | 5/1996 | Johnston et al. ............ 604/378 |
| 5,534,576 A | 7/1996 | Grot ............................ 524/377 |
| 5,571,410 A | 11/1996 | Swedberg et al. ........ 210/198.2 |
| 5,583,211 A | 12/1996 | Coassin et al. ............. 536/23.1 |
| 5,601,678 A | 2/1997 | Gerber et al. ............... 156/150 |
| 5,628,735 A | 5/1997 | Skow ......................... 604/317 |
| 5,635,358 A | 6/1997 | Wilding et al. .............. 435/7.2 |
| 5,637,469 A | 6/1997 | Wilding et al. ............ 435/7.21 |
| 5,641,400 A | 6/1997 | Kaltenbach et al. ..... 210/198.2 |
| 5,645,702 A | 7/1997 | Witt et al. ................... 204/501 |
| 5,651,888 A | 7/1997 | Shimizu et al. ........ 210/321.64 |
| 5,658,413 A | 8/1997 | Kaltenbach et al. ..... 156/272.8 |
| 5,658,802 A | 8/1997 | Hayes et al. ................. 436/518 |
| 5,691,846 A | 11/1997 | Benson, Jr. et al. ........ 359/530 |
| 5,692,263 A | 12/1997 | Sorenson ................... 15/415.1 |
| 5,698,299 A | 12/1997 | Schmidt et al. |
| 5,703,633 A | 12/1997 | Gehrer et al. ................. 347/86 |
| 5,705,813 A | 1/1998 | Apffel et al. ................ 250/288 |
| 5,707,799 A | 1/1998 | Hansmann et al. ............. 435/6 |
| 5,716,778 A | 2/1998 | Weng et al. .................... 435/4 |
| 5,716,825 A | 2/1998 | Hancock et al. ........... 45/286.5 |
| 5,721,435 A | 2/1998 | Troll .......................... 250/559 |
| 5,726,026 A | 3/1998 | Wilding et al. ............ 435/7.21 |
| 5,728,446 A | 3/1998 | Johnston et al. ............ 428/167 |
| 5,737,457 A | 4/1998 | Saini et al. .................... 385/12 |
| 5,750,015 A | 5/1998 | Soane et al. ................ 204/454 |
| 5,755,942 A | 5/1998 | Zanzucchi et al. .......... 204/454 |
| 5,757,482 A | 5/1998 | Fuchs et al. ................. 356/246 |
| 5,842,787 A | 12/1998 | Kopf-Sill et al. ........... 366/340 |
| 5,885,470 A | 3/1999 | Parce et al. .................... 216/33 |
| 5,932,315 A | 8/1999 | Lum et al. .................. 428/172 |
| 5,952,173 A | 9/1999 | Hansmann et al. ............. 435/6 |

FOREIGN PATENT DOCUMENTS

| | | |
|---|---|---|
| GB | 1 338 579 | 11/1973 |
| GB | 1 354 502 | 5/1974 |
| GB | 1 418 635 | 12/1975 |
| WO | WO 89/04628 | 6/1989 |
| WO | WO92/08972 | 5/1992 |
| WO | WO 93/11727 | 6/1993 |
| WO | WO 96/04547 | 2/1996 |
| WO | WO 96/10747 | 4/1996 |
| WO | WO 97/02357 | 1/1997 |
| WO | WO 97/13633 | 4/1997 |
| WO | WO 98/00231 | 1/1998 |
| WO | WO98/21626 | 5/1998 |
| WO | WO 98/23957 | 6/1998 |
| WO | WO 98/24544 | 6/1998 |
| WO | WO 98/46438 | 10/1998 |
| WO | WO 99/06589 | 2/1999 |
| WO | WO99/19717 | 4/1999 |

OTHER PUBLICATIONS

Article: "For Lab Chips, the Future is Plastic," *IVD Technology Magazine,* May, 1997.

Article: Roberts et al., "UV Laser Machined Polymer Substrates for the Development of Microdiagnostic Systems," *Analytical Chemistry,* vol. 69, Nov. 11, Jun. 1, 1997, pp. 2035–2042.

Article: McCormick et al., "Microchannel Electrophoretic Separation of DNA in Injection–Molded Plastic Substrates," *Analytical Chemistry,* vol. 69, Nov. 14, Jul. 15, 1997, pp. 2626–2630.

METHODS OF MANUFACTURING MICROFLUIDIC ARTICLES

FIELD OF THE INVENTION

This invention relates to microfluidic articles and methods of manufacturing same.

BACKGROUND OF THE INVENTION

There has been a drive towards reducing the size of instrumentation used for analyzing and otherwise manipulating fluid samples such as biological fluid samples. The reduced size offers several advantages, including the ability to analyze very small samples, increased analytical speed, the ability to use reduced amounts of reagents, and reduced overall cost.

Various devices for microfluid applications have been proposed. These devices typically include a glass or silicon substrate having a lithographically patterned and etched surface provided with one or more structures forming a microfluid processing architecture. Plastic substrates such as polyimides, polyesters, and polycarbonates have been proposed as well.

SUMMARY OF THE INVENTION

There is a need for polymer-based microfluidic articles that can be produced efficiently in commercial-scale quantities, e.g., in the form of a roll good, and that can be selectively tailored to perform a variety of functions, including analytical functions. Accordingly, in a first aspect the invention features a process for preparing a molded article that includes bringing a moldable material and the surface of an open molding tool into line contact with each other to imprint a microfluid processing architecture onto the moldable material. The resulting molded article is then separated from the molding surface of the tool.

A "microfluid processing architecture" refers to one or more fluid-processing structures arranged in a predetermined, self-contained pattern. Preferably, the architecture includes at least one structure having a dimension no greater than about 1000 micrometers. Moreover, fluid preferably enters and exits the architecture in the z-direction (i.e., the direction perpendicular to the plane of the architecture). For purposes of this invention, examples of suitable microfluid processing architectures include structures selected from the group consisting of microchannels, fluid reservoirs, sample handling regions, and combinations thereof.

An "open molding tool" is a molding tool that lacks a sealed cavity found in closed molds, e.g., of the type used in injection molding.

By "line contact" it is meant that the point at which the tool contacts the moldable material is defined by a line that moves relative to both the tool and the moldable material.

In one embodiment, the moldable material is an embossable polymeric substrate. The microfluid processing architecture pattern is embossed onto the surface of the polymeric substrate to create the molded article.

In another embodiment, the moldable material is a flowable resin composition. One example of such a composition is a curable resin composition, in which case the process includes exposing the composition to thermal or actinic radiation prior to separating the molded article from the molding surface to cure the composition. As used herein, "cure" and "curable resin composition" include crosslinking an already-polymerized resin, as well as polymerizing a monomeric or oligomeric composition, the product of which is not necessarily a crosslinked thermoset resin. An example of a preferred curable resin composition is a photopolymerizable composition which is cured by exposing the composition to actinic radiation while in contact with the molding surface.

Another example of a flowable resin composition is a molten thermoplastic composition which is cooled while in contact with the molding surface to solidify it.

There are two preferred molding processes in the case where the moldable material is a flowable resin composition. According to one preferred process, the flowable resin composition is introduced onto a major surface of a polymeric substrate, and the substrate and molding tool are moved relative to each other to bring the tool and flowable resin composition into line contact with each other. The net result is a two-layer structure in which a microfluid processing architecture-bearing layer is integrally bonded to the polymeric substrate.

A second preferred molding process where the moldable material is a flowable resin composition involves introducing the flowable resin composition onto the molding surface of the molding tool. A separate polymeric substrate may be combined with the flowable resin composition to create a two-layer structure in which a microfluid processing architecture-bearing substrate is integrally bonded to the polymeric substrate.

A substrate may be bonded to the molded article to form a cover layer overlying the microfluid processing architecture. Preferably, the substrate is a polymeric substrate. The molded article may also be provided with one or more microelectronic elements, microoptical elements, and/or micromechanical elements. These microelements may be incorporated in a variety of ways, illustrating the flexibility of the overall process. For example, where the moldable material is an embossable polymeric substrate, that substrate may include the microelements. Where the moldable material is a flowable resin composition and the process involves combining the resin composition with a polymeric substrate during molding, that polymeric substrate may include the microelements. It is also possible to include the microelements in the cover layer. The microelements may also be provided in the form of a separate substrate (preferably a polymeric substrate) that is bonded to the molded article.

The process is preferably designed to operate as a continuous process. Accordingly, moldable material is continuously introduced into a molding zone defined by the molding tool, and the molding tool is continuously brought into line contact with the moldable material to create a plurality of microfluid processing architectures. Preferably, the continuous process yields the article in the form of a roll that includes a plurality of microfluid processing architectures. The roll can be used as is or can be divided subsequently into multiple individual devices. Additional polymeric substrates can be continuously bonded to the article. Examples include cover layers and layers bearing microelectronic, microoptical, and/or micromechanical elements.

In a second aspect, the invention features an article that includes (A) a first non-elastic, polymeric substrate having a first major surface that includes a microfluid processing architecture (as defined above), and a second major surface; and (B) a second polymeric substrate that is integrally bonded to the second major surface of the first substrate. The second substrate is capable of forming a free-standing substrate in the absence of the first substrate. It provides mechanical support for the first substrate and also provides a means for incorporating additional features into the article such as microelectronic, microoptical, and/or micromechanical elements, thereby providing design flexibility.

A "non-elastic" material is a material having insufficient elasticity in the z-direction (i.e., the direction normal to the plane of the substrate) to act as a pump or valve when subjected to a cyclically varying force in the z-direction.

"Integrally bonded" means that the two substrates are bonded directly to each other, as opposed to being bonded through an intermediate material such as an adhesive.

The article preferably includes a cover layer overlying the microfluid processing architecture. The cover layer, which may be bonded to the first surface of the first substrate, preferably is a polymeric layer.

The article preferably includes one or more microelectronic, microoptical, and/or micromechanical elements. The microelements may be included in the first substrate, the second substrate, a polymeric cover layer, or a combination thereof.

In a third aspect, the invention features an article in the form of a roll that includes a first polymeric substrate having a first major surface that includes a plurality of discrete microfluid processing architectures (as defined above), and a second major surface. The article preferably includes a second polymeric substrate integrally bonded (as defined above) to the second major surface of the first substrate. The second substrate is capable of forming a free-standing substrate in the absence of the first substrate.

The article preferably includes a polymeric cover layer bonded to the first major surface of the first substrate.

The article preferably includes one or more microelectronic, microoptical, and/or micromechanical elements. The microelements may be included in the first substrate, the second substrate, a polymeric cover layer, or a combination thereof.

In a fourth aspect, the invention features an article that includes (A) a first polymeric substrate having a first major surface that includes a microfluid processing architecture (as defined above), and a second major surface; and (B) a second polymeric substrate. The second substrate has a first major surface that is integrally bonded (as defined above) to the second major surface of the first substrate, and a second major surface that includes one or more microelectronic elements and a via extending between the first and second major surfaces of the second substrate. The second substrate is capable of forming a free-standing substrate in the absence of the first substrate.

In a fifth aspect, the invention features an article that includes a first polymeric substrate having a first major surface that includes a microfluid processing architecture (as defined above), and a second major surface that includes one or more microelectronic elements and a via extending between the first and second major surfaces of the substrate.

In a sixth aspect, the invention features an article that includes (A) a first polymeric substrate having a first major surface that includes a microfluid processing architecture (as defined above), and a second major surface; and (B) a polymeric cover layer. The cover layer includes a first major surface overlying the first major surface of the substrate, and a second major surface that includes one or more microelectronic elements and a via extending between the first and second major surfaces of the cover layer.

In a seventh aspect, the invention features a method for processing a microfluid sample that includes (a) providing an article in the form of a roll comprising a first polymeric substrate having a first major surface that includes a plurality of discrete microfluid processing architectures, and a second major surface; (b) introducing a microfluid sample into one of the microfluid processing architectures; and (c) processing the sample (e.g., by analyzing the sample).

The invention provides polymeric articles useful for processing (e.g., analyzing) microfluid samples that can be continuously produced on a commercial scale in the convenient form of a roll good which can be readily stored and handled. The roll good can be used directly for processing a fluid sample, e.g., in a reel-to-reel continuous process involving injecting a different fluid into each microfluid processing architecture and then performing multiple operations. Alternatively, the roll good may be separated into a plurality of discrete devices following manufacture.

The manufacturing process offers significant design flexibility, enabling a number of processing steps to be performed in-line. For example, microelectronic, microoptical, and/or micromechanical elements can be readily incorporated into the article during manufacture in a variety of different ways, including as part of the substrate bearing the microfluid processing architecture, as part of a cover layer, or as part of a second polymeric substrate integrally bonded to the substrate. Various designs incorporating these microelements are also possible. Multilayer articles are readily prepared as well.

The molding process is sufficiently versatile to allow formation of a number of different microfluid processing architecture designs. Accordingly, articles can be manufactured to perform numerous functions, including, for example, capillary array electrophoresis, kinetic inhibition assays, competition immunoassays, enzyme assays, nucleic acid hybridization assays, cell sorting, combinatorial chemistry, and electrochromatography.

The molding process enables the preparation of microfluid processing architectures having high aspect ratio and variable aspect ratio features. This, in turn, provides structures exhibiting improved speed and resolution. For example, the depth of a microchannel can be varied while maintaining a constant microchannel width. Such microchannels can be used to construct vertically tapered inlet and outlet diffusers for a piezoelectric valve-less diffuser micropump, or used to provide electrokinetic zone control or electrokinetic focusing. Similarly, the width of a high aspect ratio microchannel can be tapered at constant depth. The resulting structure is also useful for providing electrokinetic zone control.

It is also possible to taper both the depth and width of the microchannels to provide a constant cross-sectional area or, alternatively, a constant cross-sectional perimeter. As a consequence of the constant cross-sectional area or perimeter, the resulting structure enables achievement of a constant voltage gradient throughout the length of the channel for predominantly electrophoretic flow or electroosmotic flow, thereby providing optical confinement for single molecule detection without loss of resolving power. This structure is also useful for providing a transition between low aspect ratio and high aspect ratio structures (e.g., high aspect ratio injection tees, low aspect ratio probe capture zones, microwell reactors, or piezoelectric drive elements) without loss of electrokinetic resolving power.

It is also possible to prepare two intersecting microchannels having different depths. This feature, in turn, may be exploited to create a microfluidic switch in a hydrophobic substrate. Because of the depth difference, fluid in one arm of the relatively shallow microchannel will not cross the intersection unless a buffer is introduced into the relatively deeper microchannel to bridge the intersection. The variable depth feature is also useful for preparing post arrays for corralling probe capture beads in an immunoassay or nucleic acid assay, while simultaneously permitting the reporter reagent and fluid sample to flow freely.

Other features and advantages of the invention will be apparent from the following description of the preferred embodiments thereof, and from the claims.

DETAILED DESCRIPTION

Figure 1:
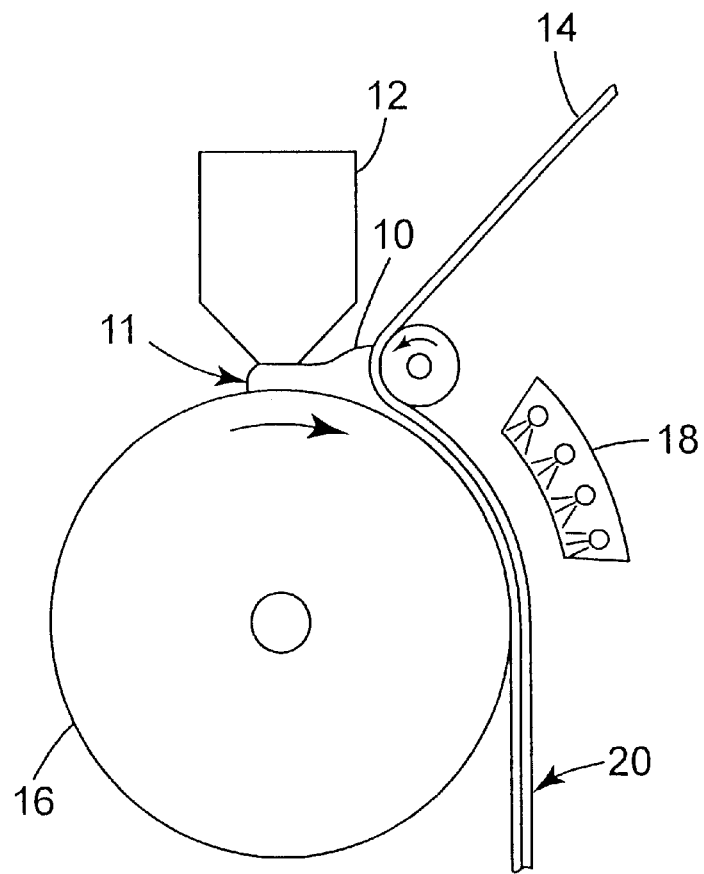
FIG. 1 is a schematic drawing of a continuous "cast and cure" process for preparing a microfluidic article.

The invention features a polymer-based, microfluid processing architecture-bearing article for processing (e.g., analyzing) microfluid samples, and a continuous roll-to-roll process for manufacturing the article. One embodiment of the process (referred to as a "continuous cast and cure" process) is shown in FIG. 1. Referring to FIG. 1, a flowable, preferably essentially solvent-free, photocurable resin composition 10 is extruded from a die 12 onto the surface of a continuous, flexible, optically transparent substrate 14.

Examples of suitable materials for substrate 14 include poly(methylmethacrylate) polycarbonates, polyesters, and polyimides. Examples of suitable photocurable resin compositions include alkyl acrylates and methacrylates (e.g., polymethyl methacrylate). The composition also includes a photoinitiator. Examples of suitable photoinitiators include benzoin ethers such as benzoin methyl ether and benzoin isopropyl ether; substituted acetophenones such as 2,2-diethyoxacetophenone, 2,2-dimethoxy-2-phenyl-1-phenylacetophenone, and dimethoxyhydroxyacetophenone; substituted alpha-ketols such as 2-methyl-2-hydroxy propiophenone; aromatic sulfonyl chlorides such as 2-naphthalene sulfonyl chloride; and photoactive oximes such as 1-phenyl-1,2-propanedione-2(O-ethoxycarbonyl) oxime. Other ingredients which may be incorporated in the composition include monohydroxy and polyhydroxy compounds, thixotropic agents, plasticizers, toughening agents, pigments, fillers, abrasive granules, stabilizers, light stabilizers, antioxidants, flow agents, bodying agents, flatting agents, colorants, binders, blowing agents, fungicides, bactericides, surfactants, glass and ceramic beads, and reinforcing materials such as woven and non-woven webs of organic and inorganic fibers.

Resin 10 and substrate 14 are brought into contact with the molding surface of a molding tool 16 for imprinting a desired microfluid processing architecture pattern onto the surface of resin layer 10. As shown in FIG. 1, molding tool 16 is in the form of a roll or endless belt that rotates in a clockwise direction. However, it may also take the form of a cylindrical sleeve. The molding tool may be prepared using a variety of mastering techniques, including laser ablation mastering, electron beam milling, photolithography, x-ray lithography, machine milling, and scribing. It bears a pattern of the desired microfluid processing architecture.

Figure 10A:
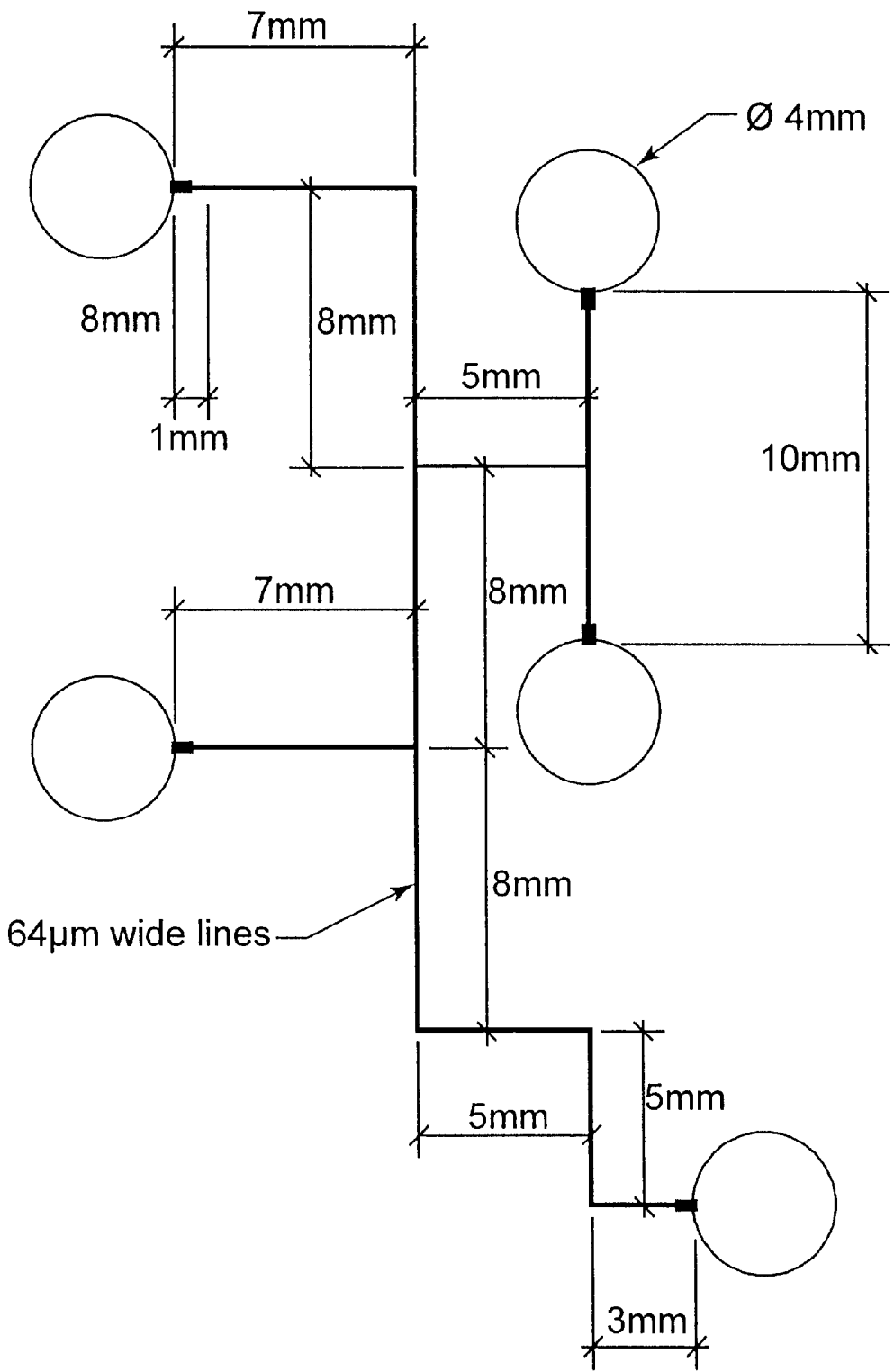
FIGS. 10(a) and 10(b) are schematic drawings showing representative microfluid processing architecture designs.
Figure 10B:
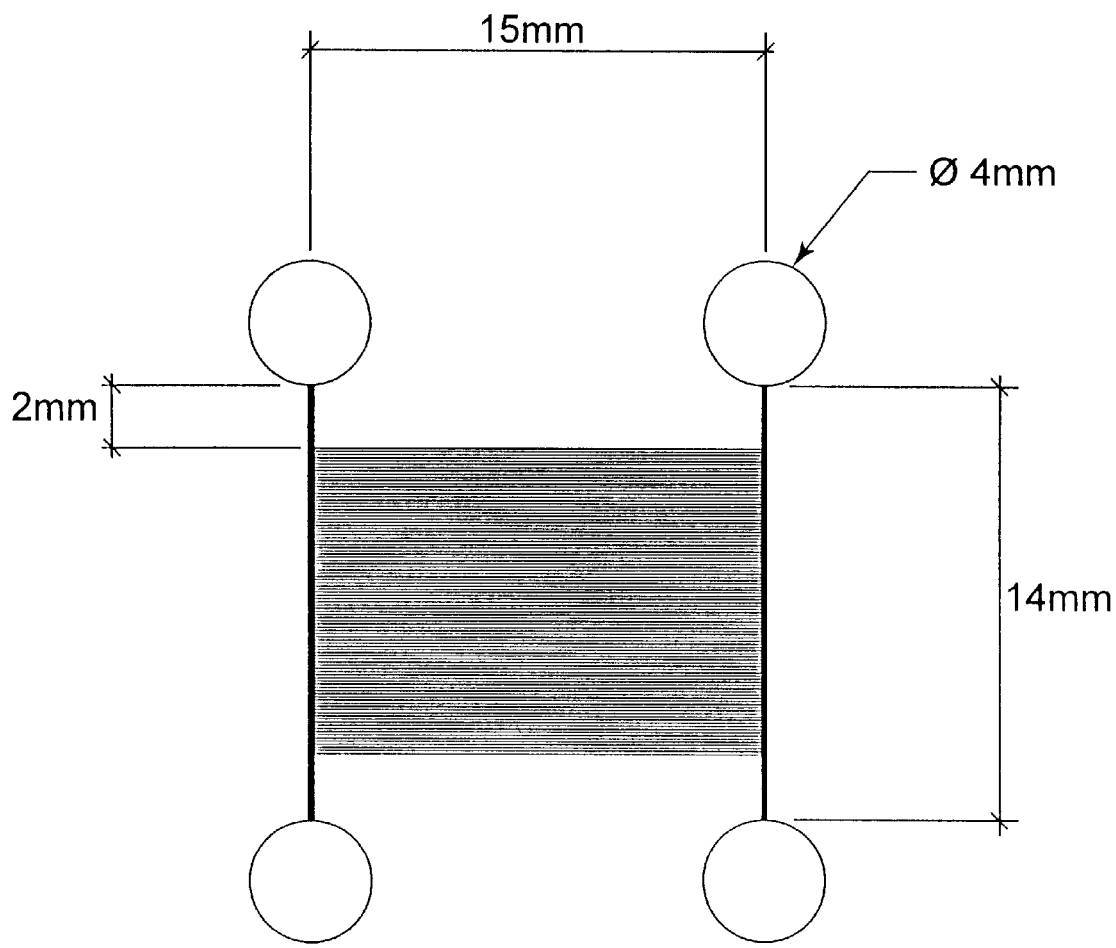
Figure 11A:
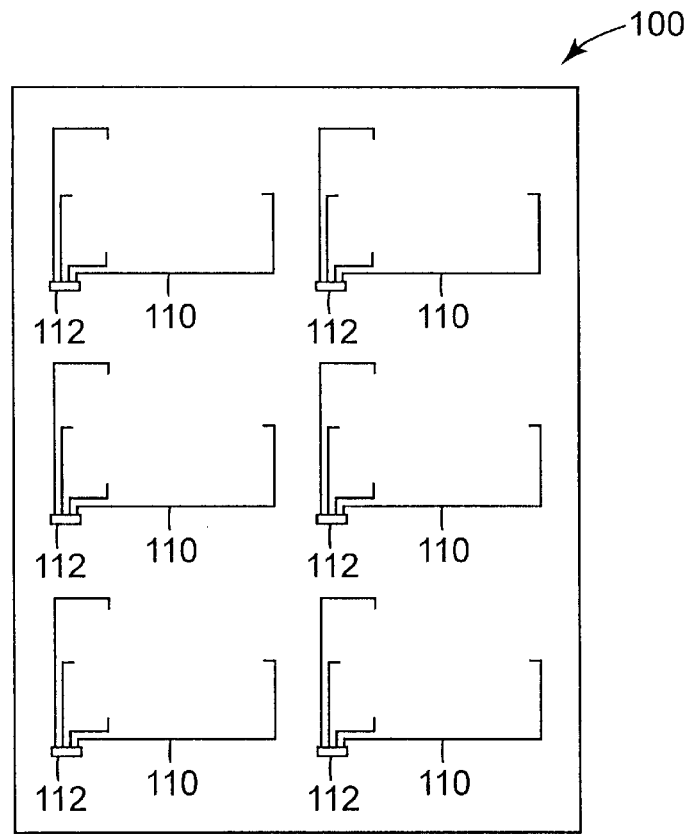
FIG. 11(a) is a top view of a flexible polymeric substrate featuring a plurality of electrically conductive traces and contact pads.
Figure 11B:
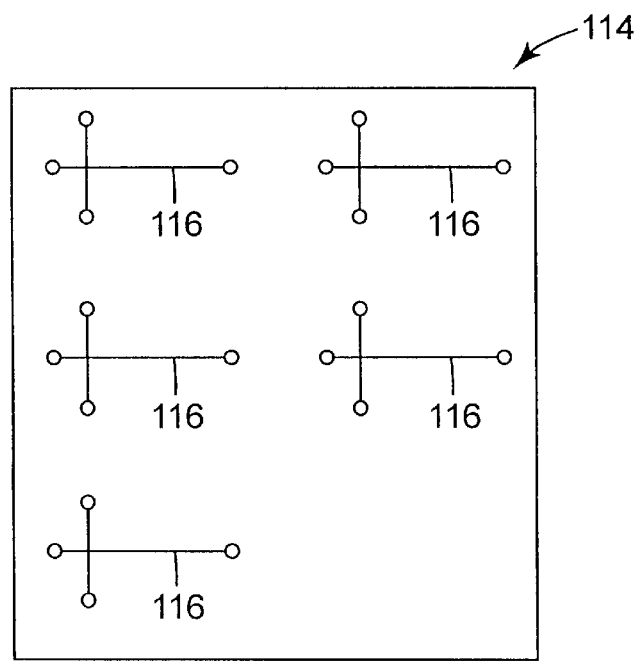
FIG. 11(b) is a top view of a flexible polymeric substrate featuring a plurality of microfluid processing architectures on a major surface of the substrate.

The particular architecture design is selected based upon the desired operation which the article is intended to perform. Representative designs are shown in FIGS. 10(a), 10(b) and 11(b). The designs include a competition assay chip (FIG. 10(a)) and a ladder chip (FIG. 10(b)) and an electrophoresis chip (FIG. 11(b)). The architectures feature various combinations of microchannels, fluid reservoirs, and sample handling regions. The dimensions for the individual microarchitectural structures shown in FIGS. 10(a) and (b) are representative of typical dimensions used for such chips. The particular dimensions for any given chip may vary.

Resin layer 10 is brought into line contact with the rotating surface of molding tool 16. The line 11 is defined by the upstream edge of resin layer 10 and moves relative to both tool 16 and resin layer 10 as tool 16 rotates. Substrate 14 remains in contact with resin layer 10 as the latter contacts the surface of molding tool 16. Any excess resin is minimized, after which tool 16, substrate 14, and resin layer 10 are exposed to actinic radiation from a radiation source 18, preferably in the form of ultraviolet radiation, to cure the resin composition while it remains in contact with the molding surface of tool 16. The exposure time and dosage level are selected based upon the characteristics of the individual resin composition, including the thickness of resin layer 10.

Figure 1A:
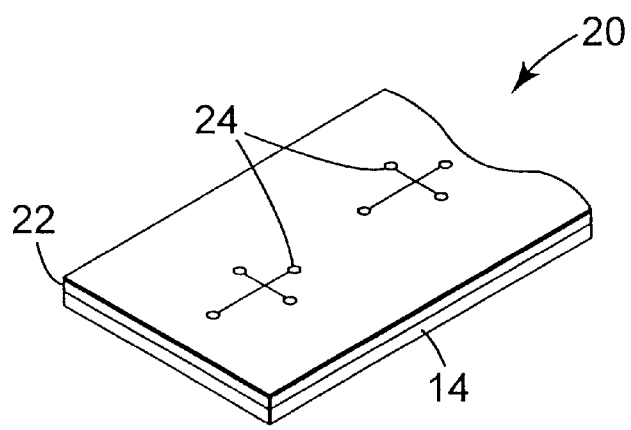
FIG. 1(a) is a perspective drawing of a microfluidic article prepared according to the process shown in FIG. 1.

As shown in FIG. 1(a), the resulting product 20 is in the form of a two layer sheet featuring a polymeric substrate 22 bearing a plurality of microfluid processing architectures 24 integrally bonded to substrate 14. Following molding, the sheet may be taken up on a roll (not shown) to yield the product in the form of a roll good.

It is also possible to perform the cast and cure process using a thermally curable resin composition as the moldable resin composition, in which case a source of thermal radiation (e.g., a heat lamp), rather than actinic radiation, is employed.

In a variation of this process, a molten thermoplastic resin is used as the moldable resin composition. The combination of the tool and resin is cooled following contact to solidify (rather than cure) the resin.

Figure 2:
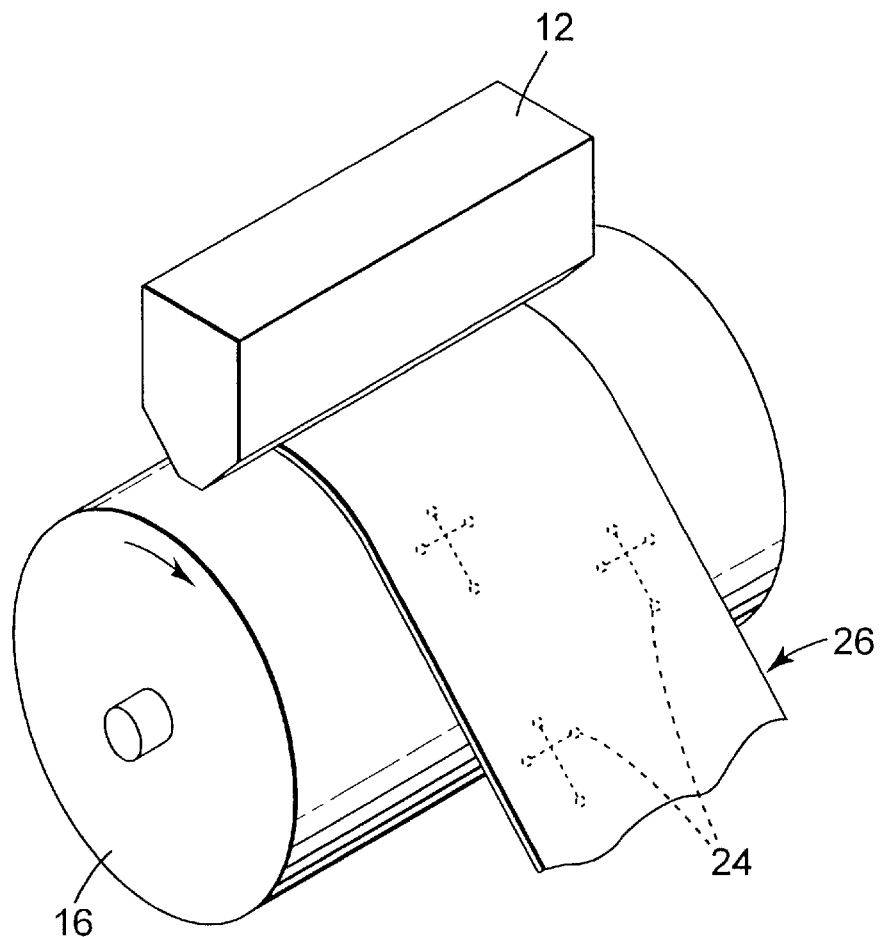
FIG. 2 is a perspective drawing of a continuous "extrusion embossing" process for preparing a microfluidic article.
Figure 2A:
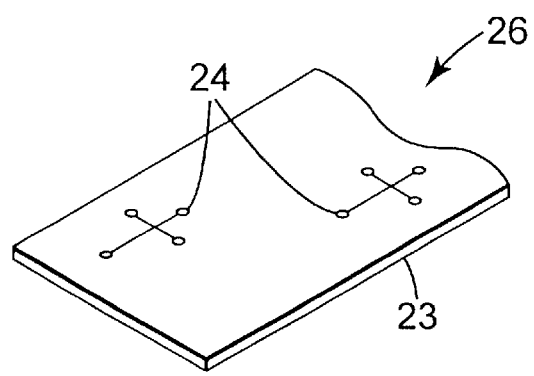
FIG. 2(a) is a perspective drawing of a microfluidic article prepared according to the process shown in FIG. 2.

Microfluidic articles may also be prepared according to an extrusion embossing process. Various embodiments of this process are shown in FIGS. 2–5. Referring to FIG. 2, a flowable resin composition is extruded from die 12 directly onto the rotating surface of molding tool 16 such that resin is brought into line contact with the rotating surface of molding tool 16; examples of suitable resin compositions include the photocurable, thermally curable, and thermoplastic resin compositions described above. The line is defined by the upstream edge of the resin and moves relative to both tool 16 and the resin as tool 16 rotates. As shown in FIG. 2(a), the resulting product is a single layer article 26 in the form of a sheet featuring a polymeric substrate 23 bearing a plurality of microfluid processing architectures 24. The sheet may be taken up on a roll (not shown) to yield the article in the form of a roll good.

Figure 3:
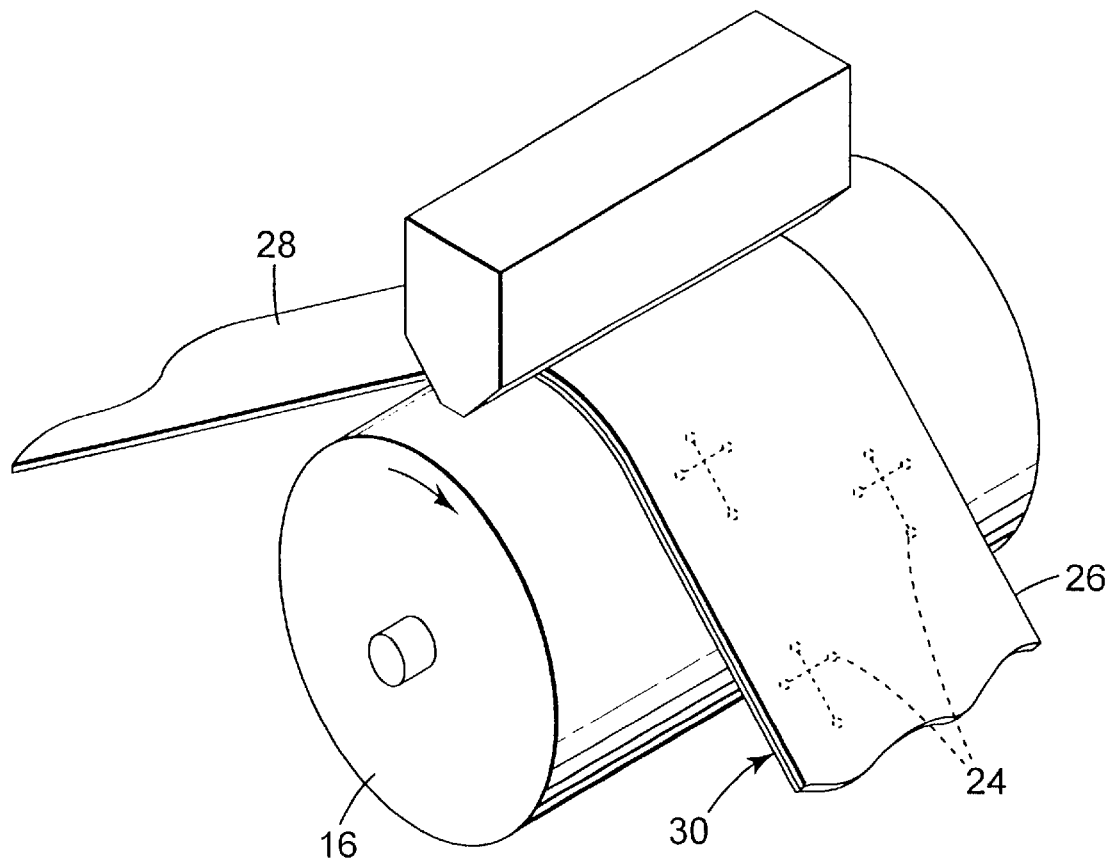
FIG. 3 is a perspective drawing of a second embodiment of a continuous "extrusion embossing" process for preparing a microfluidic article.
Figure 3A:
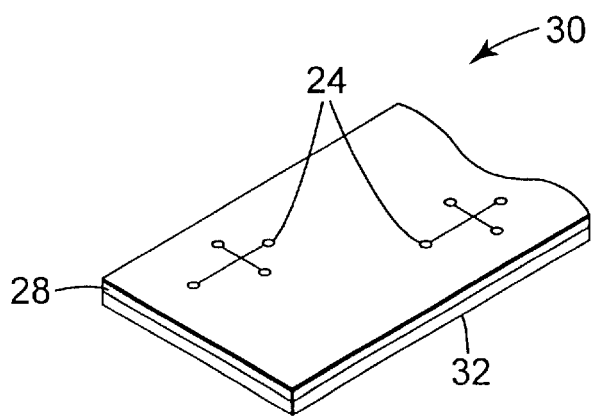
FIG. 3(a) is a perspective drawing of a microfluidic article prepared according to the process shown in FIG. 3.

FIG. 3 illustrates another variation of the extrusion embossing process shown in FIG. 2. As shown in FIG. 3, a polymeric substrate 28 is introduced into a molding zone defined by tool 16 and brought into line contact with the rotating molding surface of tool 16. Suitable materials for substrate 28 include those described above for substrate 14. Non-optically transparent substrates may be used as well. A flowable resin composition (as described above) is extruded from die 12 onto the surface of substrate 28 opposite the surface of substrate 28 in line contact with the molding surface of tool 16. Molding tool 16 embosses a plurality of microfluid processing architectures onto the surface of substrate 28. The resulting article, as shown in FIG. 3(a), is an article in the form of a two-layer sheet 30 featuring a polymeric substrate 28 bearing a plurality of microfluid processing architectures 24 that is integrally bonded to a polymeric layer 32 formed from the resin extruded onto substrate 28. Following molding, the sheet may be taken up on a roll (not shown) to yield the product in the form of a roll good.

Figure 4:
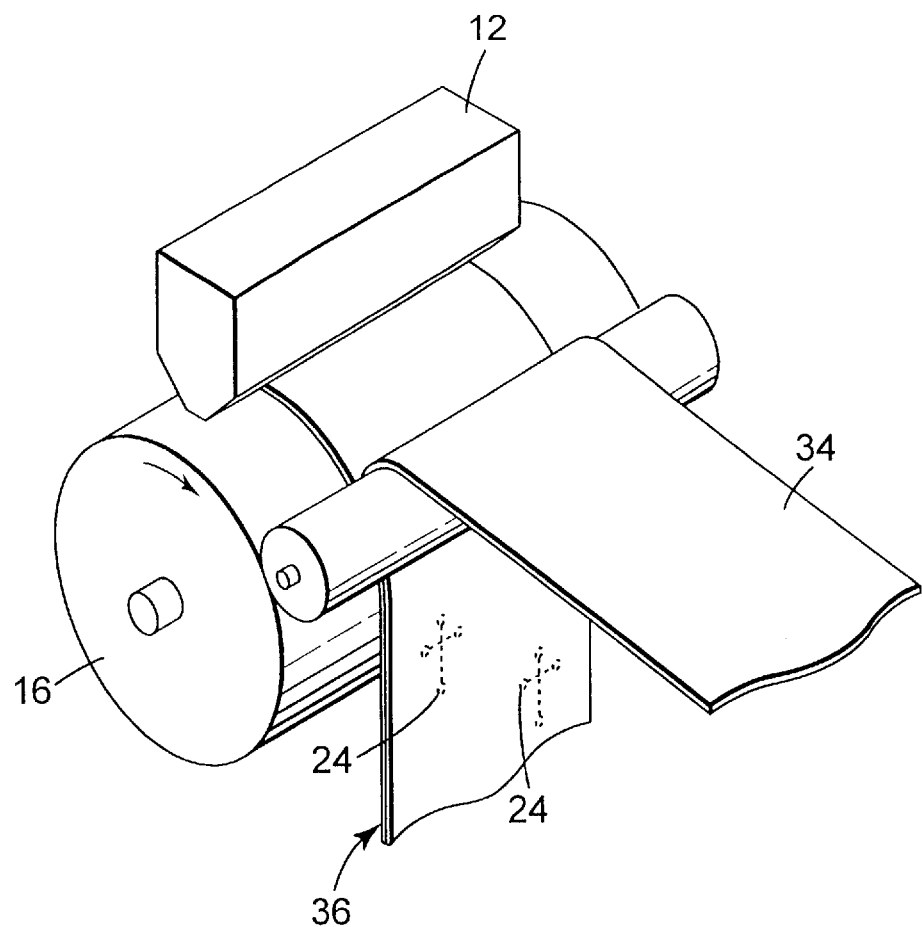
FIG. 4 is a perspective drawing of a third embodiment of a continuous "extrusion embossing" process for preparing a microfluidic article.
Figure 4A:
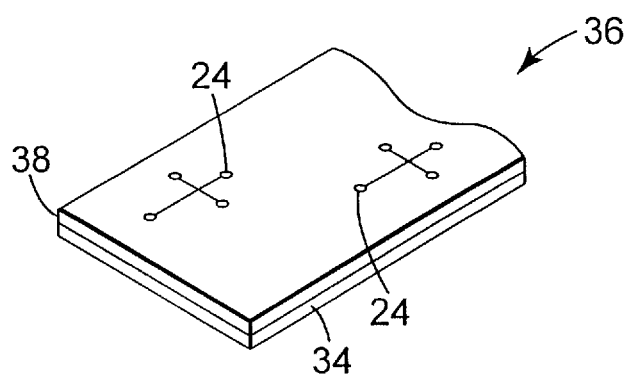
FIG. 4(a) is a perspective drawing of a microfluidic article prepared according to the process shown in FIG. 4.

FIG. 4 illustrates yet another variation of the extrusion embossing process shown in FIG. 2. As shown in FIG. 4, a flowable resin composition (as described above) is extruded from die 12 onto the rotating surface of molding tool 16 such that resin is brought into line contact with the rotating surface of molding tool 16. As in the case of the embodiment shown in FIG. 2, the line is defined by the upstream edge of the resin and moves relative to both tool 16 and the resin as tool 16 rotates. At the same time, a second polymeric substrate 34 is introduced into the molding zone defined by tool 16 such that it contacts the resin. Suitable materials for substrate 34 include the materials discussed above in the context of substrate 14. Non-optically transparent substrates may also be used. The resulting article is in the form of a two-layer sheet 36 featuring a polymeric substrate 38 bearing a plurality of microfluid processing architectures 24 that is integrally bonded to polymeric substrate 34. Following molding, the sheet may be taken up on a roll (not shown) to yield the product in the form of a roll good.

Figure 5:
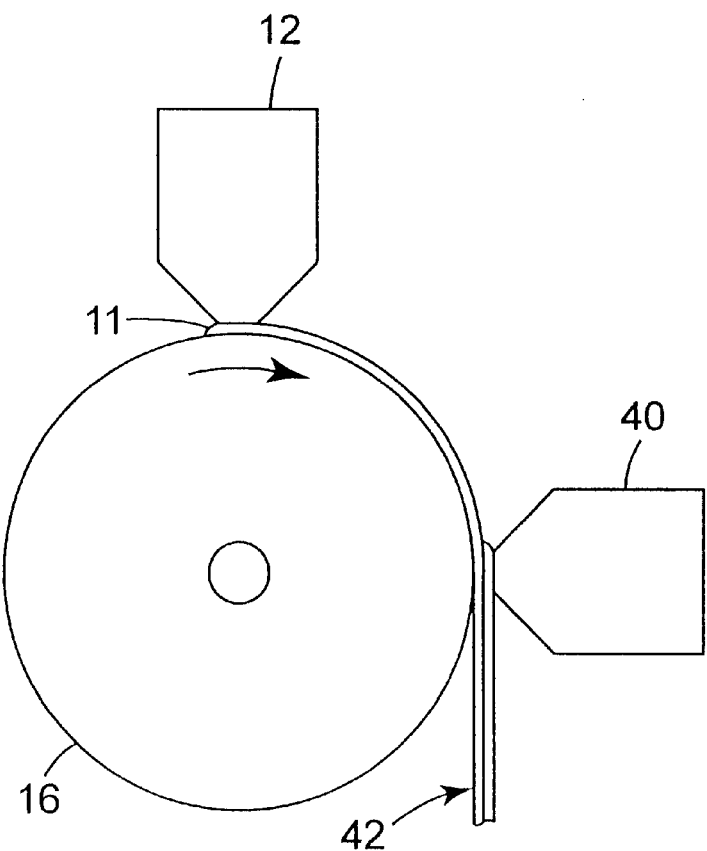
FIG. 5 is a schematic drawing of a fourth embodiment of a continuous "extrusion embossing" process for preparing a microfluidic article.
Figure 5A:
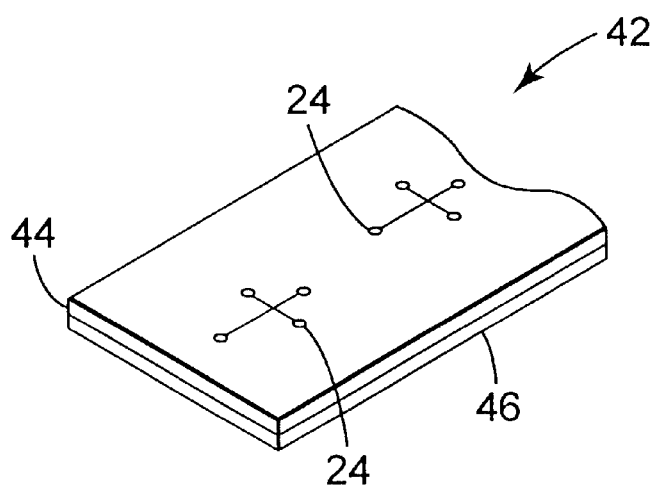
FIG. 5(a) is a perspective drawing of a microfluidic article prepared according to the process shown in FIG. 5.

FIG. 5 illustrates yet another embodiment of an extrusion embossing process. As shown in FIG. 5, a flowable resin composition (as described above) is extruded from die 12 onto the rotating surface of molding tool 16 such that resin is brought into line contact with the rotating surface of molding tool 16. As in the case of the embodiment shown in FIG. 2, the line is defined by the upstream edge of the resin and moves relative to both tool 16 and the resin as tool 16 rotates. Additional resin from a second die 40 is extruded onto the layer of resin in contact with molding tool 16.

The resulting product is a two-layer article 42 in the form of a sheet featuring a polymeric substrate 44 bearing a plurality of microfluid processing architectures 24 that is integrally bonded to a polymeric substrate 46 formed from the resin extruded from die 40. Following molding, the sheet may be taken up on a roll (not shown) to yield the product in the form of a roll good. It is also possible to form additional polymeric layers by incorporating additional extrusion dies. Alternatively, a single die equipped with an appropriate feedblock may be used to co-extrude multiple polymeric layers.

Figure 6:
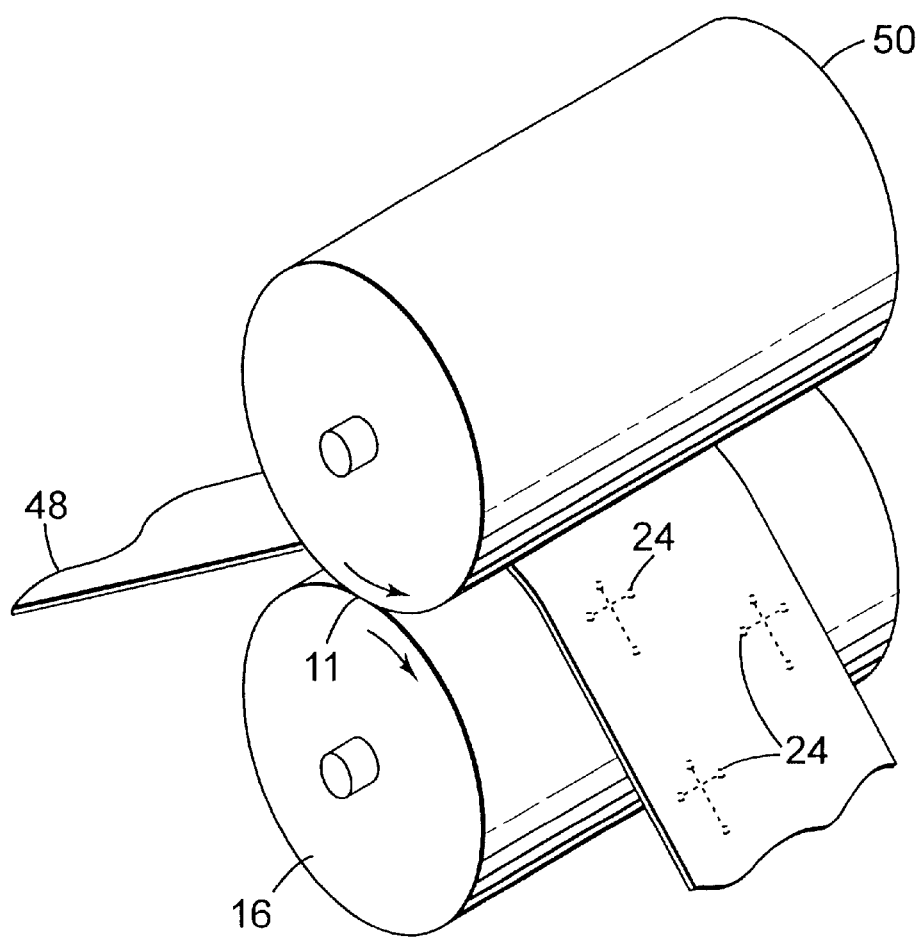
FIG. 6 is a perspective drawing of a continuous "substrate embossing" process for preparing a microfluidic article.

In yet another embodiment, articles may be prepared by a substrate embossing process. As illustrated in FIG. 6, a single, embossable substrate 48 is brought into line contact with molding tool 16 to form the microfluid processing architecture directly on the surface of the substrate. The line 11 is formed by the intersection of (a) the upstream edge of substrate 48 and (b) the nip formed between roller 50 and the rotating surface of molding tool 16. Optionally, roller 50 can have a molding surface bearing a microfluid processing architecture pattern. The resulting article features a substrate having a plurality of microfluid processing architectures on both of its major surfaces.

Figure 6A:
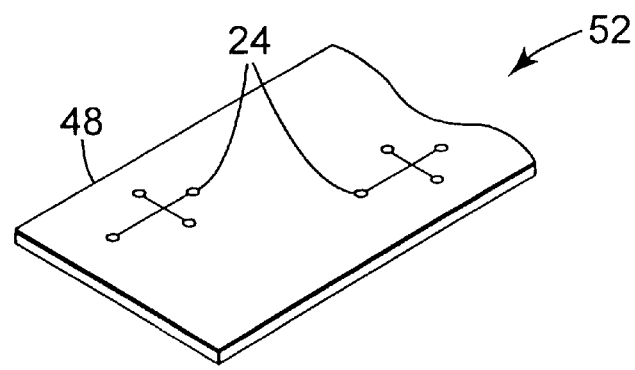
FIG. 6(a) is a perspective drawing of a microfluidic article prepared according to the process shown in FIG. 6.

As shown in FIG. 6(a), the resulting product is a single layer article 52 in the form of a sheet featuring a polymeric substrate 48 bearing a plurality of microfluid processing architectures 24. The sheet may be taken up on a roll (not shown) to yield the article in the form of a roll good.

Figure 7:
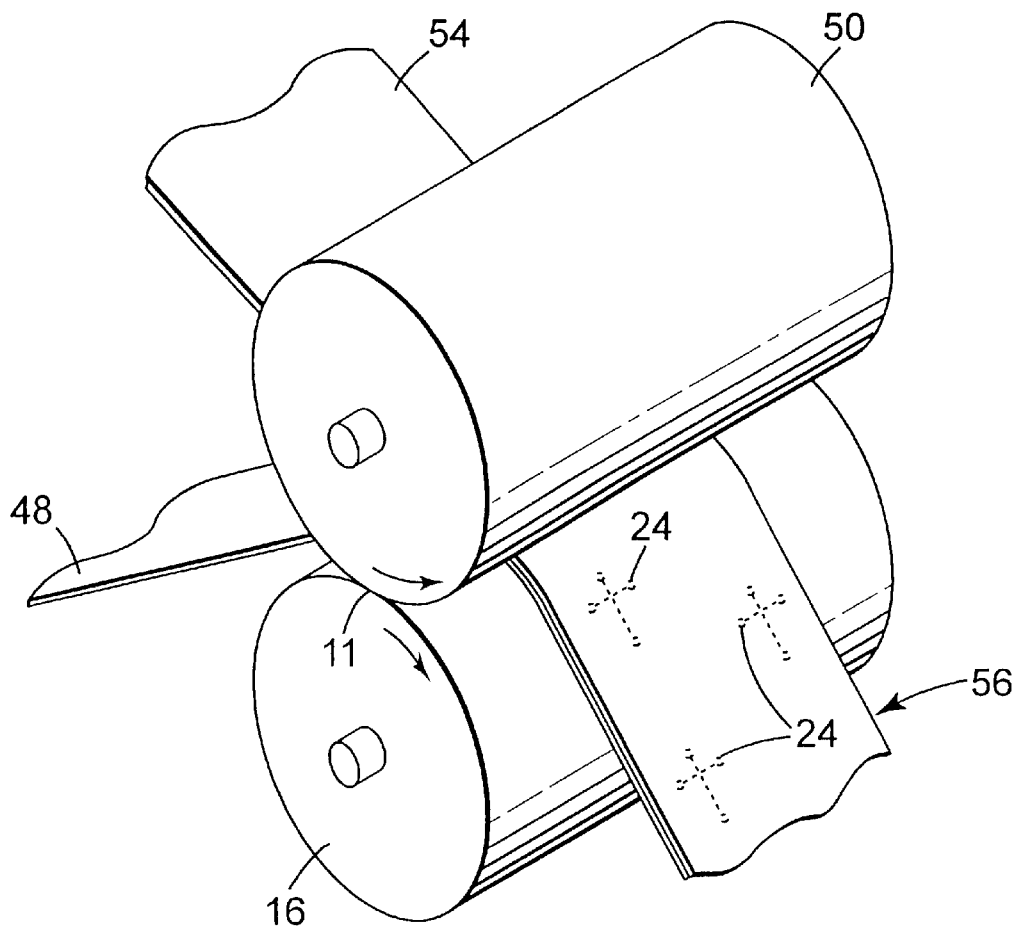
FIG. 7 is a perspective drawing of a second embodiment of a "substrate embossing" process for preparing a microfluidic article.

FIG. 7 illustrates a variation of the embossing process illustrated in FIG. 6. As shown in FIG. 7, embossable substrate 48 is brought into line contact with molding tool 16 to form the microfluid processing architecture directly on the surface of the substrate. The line 11 is formed by the intersection of (a) the upstream edge of substrate 48 and (b) the nip formed between roller 50 plus a second polymeric substrate 54 and the rotating surface of molding tool 16. Substrate 54 is positioned such that it contacts the surface of substrate 48 opposite the surface in contact with the molding surface of tool 16.

Figure 7A:
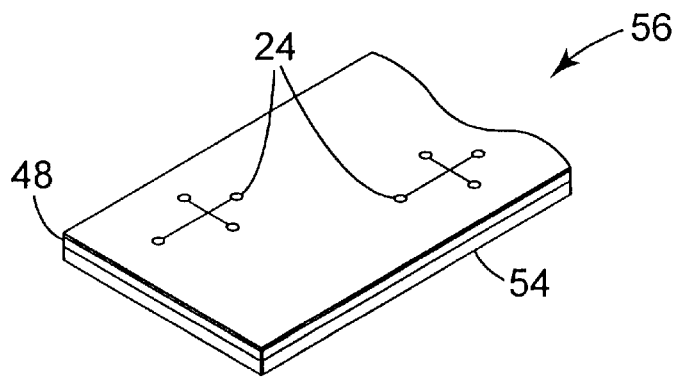
FIG. 7(a) is a perspective drawing of a microfluidic article prepared according to the process shown in FIG. 7.

The resulting article, shown in FIG. 7a, is a two-layer article 56 in the form of a sheet featuring a polymeric substrate 48 bearing a plurality of microfluid processing architectures 24 that is integrally bonded to a polymeric substrate 54. The sheet may be taken up on a roll (not shown) to yield the article in the form of a roll good.

Following molding the article is in the form of a "blank" that can be taken up by a take-up roller and stored. To assemble an operable microfluid processing device, the blank is combined with a separate cover layer that overlies the microfluid processing architecture-bearing layer. In this form, the device is useful for processing (e.g., analyzing) microfluid samples.

Materials for the cover layer are capable of forming a fluid-tight seal with the microfluid processing architecture-bearing substrate. In addition, they resist degrading in the presence of reagents such as buffers typically used for sample analysis, and preferably minimize background fluorescence and absorption; the latter feature is particularly useful when the device is to be used in conjunction with fluorescence-based analytical techniques.

The cover layer may take the form of a polymeric substrate that is bonded to the microfluid processing architecture-bearing surface of the substrate. Examples of suitable polymeric substrates include polycarbonate, polyester, poly(methylmethacrylate), polyethylene, and polypropylene. Bonding may be effected using a pressure sensitive adhesive (e.g., a styrene-butadiene-styrene block copolymer adhesive commercially available from Shell under the designation "Kraton" rubber), a hot melt adhesive (e.g., ethylene-vinyl acetate adhesives), a patterned adhesive, or a thermoset adhesive (e.g., epoxy adhesives). The adhesive may be laid down in the form of a pattern such that bonding occurs at discrete locations on substrate 20. Bonding may also be effected by laminating or solvent welding the cover layer directly to the microfluid processing architecture-bearing substrate.

Rigid cover layers such as glass cover layers may be used as well. In addition, the cover layer may be part of the analytical instrumentation with which the article is designed to be used.

Figure 8:
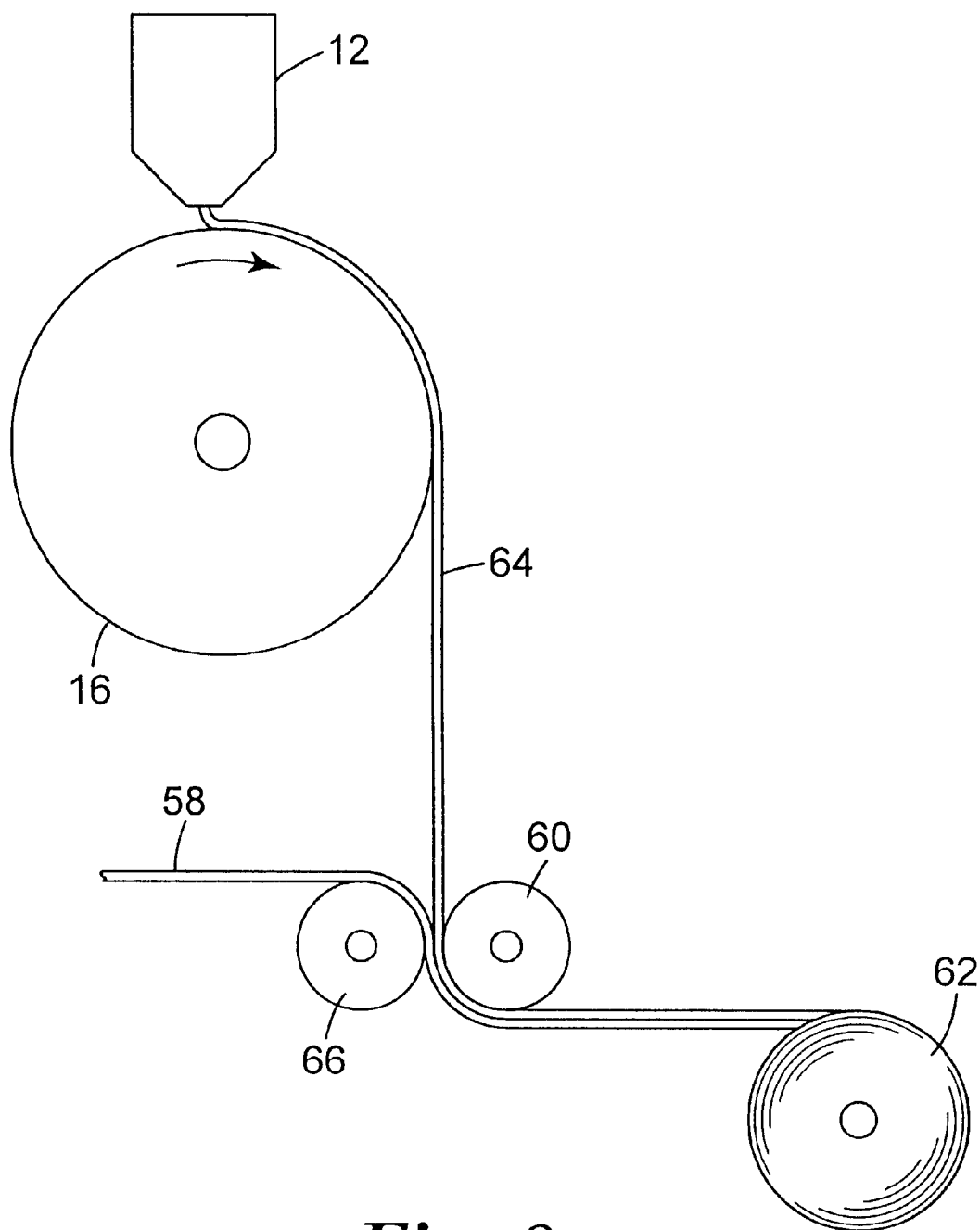
FIG. 8 is a schematic drawing of a continuous process for preparing a microfluidic article in which a cover layer is laminated to a microfluid architecture-bearing substrate following molding.

FIG. 8 illustrates a preferred method for adding a cover layer in-line to a microfluid processing architecture bearing substrate 64. As shown in FIG. 8, article 64 is conveyed to a lamination zone located downstream of the molding zone. The lamination zone includes a flexible, polymeric cover substrate 58 on a roller 66. Within the lamination zone, cover substrate 58 is laminated to article 64 between rollers 60, 66.

Although all of the above-described articles feature a single substrate with a plurality of microfluid processing architectures on one or both of its major surfaces, it is also possible to prepare articles featuring layers of such substrates bonded together. One way to produce such a multi-layered article would be to substitute a microfluid processing architecture-bearing substrate for the cover substrate shown in FIG. 8.

Thin film inorganic coatings may be selectively deposited on portions of the microfluid processing architectures, e.g., on the interior surface of microchannels. Deposition may occur either in-line during manufacture or in a subsequent operation. Examples of suitable deposition techniques include vacuum sputtering, electron beam deposition, solution deposition, and chemical vapor deposition.

The inorganic coatings may perform a variety of functions. For example, the coatings may be used to increase the hydrophilicity of the microfluid processing architecture or to improve high temperature properties. Application of certain coatings may facilitate wicking a sizing gel into the microchannels of an electrophoresis device. Conductive coatings may be used to form electrodes or diaphragms for piezoelectric or peristaltic pumping. Coatings may be used as barrier films to prevent outgassing for applications such as gas chromatography.

It is also possible to selectively deposit reagents, biological probes, biocompatible coatings, and the like onto various portions of the microfluid processing architecture. Alternatively, these materials may be deposited in a predetermined pattern on the surface of the cover layer designed to contact the microfluid processing architecture.

The article preferably includes one or more microelectronic, microoptical, and/or micromechanical elements as well. Examples of microelectronic elements include conductive traces, electrodes, electrode pads, micro-heating elements, electrostatically driven pumps and valves, microelectromechanical systems (MEMS), and the like. Examples of microoptical elements include optical waveguides, waveguide detectors, reflective elements (e.g., prisms), beam splitters, lens elements, solid state light sources and detectors, and the like. Examples of micromechanical elements include filters, valves, pumps, pneumatic and hydraulic routing, and the like. The microelements may be incorporated in the cover layer, either surface of the microfluid processing architecture-bearing substrate, an additional polymeric substrate bonded to the microfluid processing architecture-bearing substrate, or a combination thereof.

The microelements serve a variety of functions. For example, microelectronic elements that make contact with fluid at particular points in the microfluid processing architecture can be designed to electrokinetically drive fluids through the architecture with a high degree of control. Such microelectronic elements can enable operations such as electrokinetic injection, capillary electrophoresis, and isoelectric focusing, as well as more complex operations such as delivering precise amounts of reagents to one or more sample handling regions for applications such as capillary array electrophoresis and combinatorial chemistry.

Microelectronic elements that contact the fluid may also be designed to form an addressable electronic matrix for free field electrophoretic sorting of charged biological species such as cells, nucleic acid fragments, and antigens. Microelectronic elements that contact the fluid at a particular point can also be used to detect species electrochemically.

It is also possible to design microelements that do not contact the fluid. For example, microelectronic elements can be designed to lie in close proximity to the microfluid processing architecture such that they can be used to heat and cool fluid samples, or to establish different temperature zones throughout the microfluid processing architecture. Such zones, in turn, are used to support thermal cycling required in applications such as PCR amplification of nucleic acids and combinatorial chemistry experiments. In addition, microelectronic elements lying in close proximity to the microfluid processing architecture can be designed to form an antenna to detect AC impedance changes useful for detecting analytes in a microfluidic separation system.

Figure 9A:
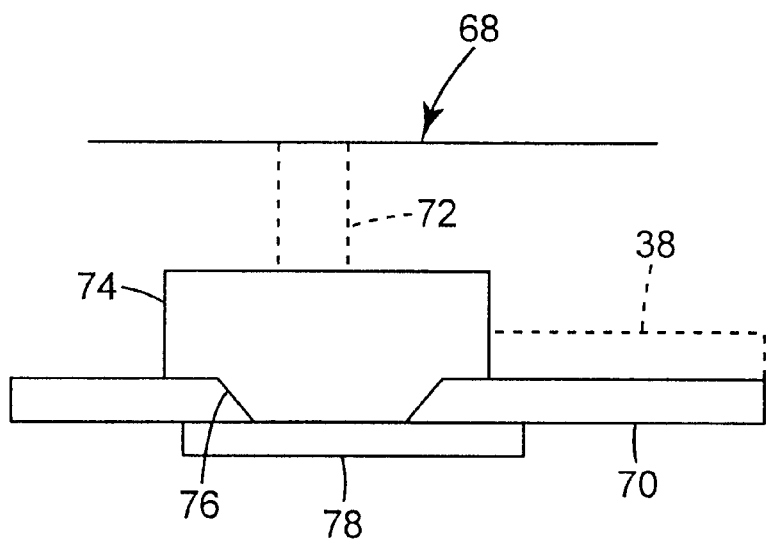
FIGS. 9(a) and 9(b) are cross-sectional views showing a microfluid processing architecture-bearing substrate combined with a cover layer provided with microelectronic elements.
Figure 9B:
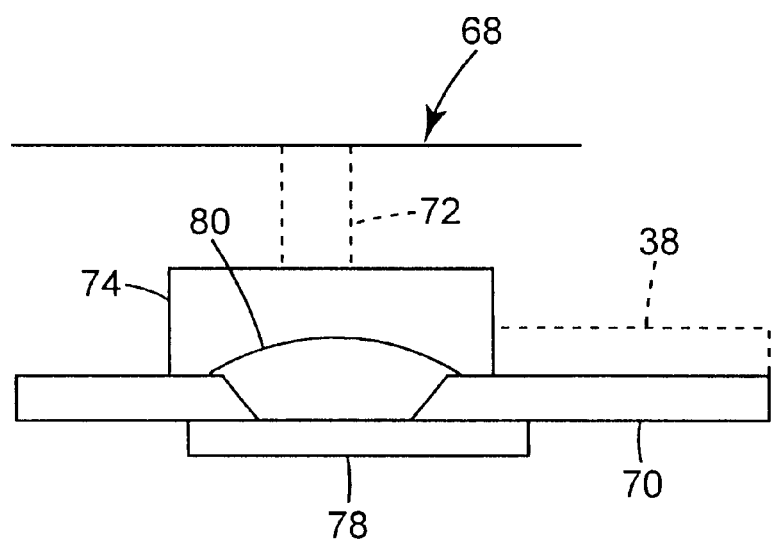

There are several different ways to incorporate microelectronic, microoptical, and/or micromechanical elements into the microfluid processing architecture-bearing articles. For example, the microelements may be incorporated into cover layer 70, which is then bonded to substrate 68 as described above. Such an arrangement involving microelectronic elements is shown in FIGS. 9(a) and 9(b). Cover layer 70 is bonded at one surface to the microfluid processing architecture-bearing surface of substrate 68. The microfluid processing architecture shown in FIGS. 9(a) and 9(b) includes an inlet port 72, a fluid reservoir 74, and a microchannel 38. Cover layer 70 features an electrically conductive via 76 in communication with reservoir 74 that terminates in a conductive circuit trace 78. Trace 78 acts as an electrode for applying a voltage to reservoir 74 to drive fluid, or components therein, throughout the microfluid processing architecture. As shown in FIG. 9(b), via 76 may be filled with metal to form an electrically conductive "bump" 80 in communication with reservoir 74.

Another method for incorporating microelectronic elements into the article involves providing a flexible polymeric substrate bearing a series of electrically conductive traces (e.g., traces made from nickel, gold, platinum, palladium, copper, conductive silver-filled inks, or conductive carbon-filled inks), and then forming the microfluid processing architecture on a surface of this substrate. Examples of suitable substrates include those described in Klun et al., U.S. Pat. No. 5,227,008 and Gerber et al., U.S. Pat. No. 5,601,678. The substrate then becomes the microfluid processing architecture-bearing substrate.

The microfluid processing architecture may be formed in several ways. For example, the conductive trace-bearing surface of the substrate may be brought into contact with a molding tool having a molding surface bearing a pattern of the desired microfluid processing architecture following the embossing process described in FIG. 6. Following contact, the substrate is embossed to form the microfluid processing architecture on the same surface as the conductive traces. The trace pattern and molding surface are designed such that the conductive traces mate with appropriate features of the microfluid processing architecture.

It is also possible, using the same molding tool, to emboss the microfluid processing architecture onto the surface of the substrate opposite the conductive trace-bearing surface. In this case, the non-trace bearing surface is provided with a series of electrically conductive vias or through holes prior to embossing to link the conductive traces with appropriate structures of the microfluid processing architecture.

Alternatively, it is possible to bond a separate polymeric substrate bearing microelectronic, microoptical, and/or micromechanical elements to the microfluid processing architecture-bearing surface of a polymeric substrate using, e.g., a patterned adhesive such that the conductive traces mate with appropriate features of the microfluid processing architecture.

It is also possible to introduce microelectronic, microoptical, and/or micromechanical elements into a separate polymeric substrate that is bonded to the microfluid processing architecture-bearing substrate following the processes described in FIGS. 1, 3, 4, and 7. To accomplish this objective, a flexible substrate having a series of electrically conductive vias and bumps on one of its major surfaces is used as substrate 14, 28, 34, or 54. Microfluid processing architecture is then molded as described above on the via and bump-bearing surface of the substrate.

It is also possible to introduce microelectronic, microoptical, and/or micromechanical elements into a separate polymeric substrate that is laminated to the microfluid processing architecture-bearing substrate subsequent to molding.

Another method for equipping the article with microelectronic, microoptical, and/or micromechanical elements involves taking a polymeric substrate having microfluid processing architecture on one surface, and inserting electrically conductive posts or pins through the opposite surface; alternatively, a z-axis electrically conductive adhesive may be used (e.g., Z-axis Adhesive Film 7303 commercially available from 3M Company of St. Paul, Minn.). The article can then be pressure mounted to a circuit board. In a variation of this process, electrically conductive posts or pins may be inserted through a cover layer overlying the microfluid processing architecture-bearing substrate for providing an electrical connection.

Yet another method for equipping the article with microelectronic, microoptical, and/or micromechanical elements involves taking a polymeric substrate having microfluid processing architecture on one surface, and depositing a pattern of electrically conductive metal traces directly onto this surface using conventional metal deposition and photolithographic techniques.

The articles may be used to perform a variety of procedures, including analytical procedures. A roll containing a number of discrete microfluid processing architectures may be used directly in a continuous reel-to-reel process. According to this process, the roll would be continuously fed to a microfluid sample dispenser which would inject a microfluid sample into the inlet port of each microfluid processing architecture. The resulting samples would then be processed (e.g., analyzed) accordingly. Alternatively, the roll may be slit to form a number of individual devices suitable for use in a batch process.

The invention will now be described further by way of the following examples.

EXAMPLES

Example 1

Two separate rolls of film, each containing a number of microfluid processing architectures, were prepared using microstructured nickel tooling in the form of an endless belt. One of the tools was designed to have the microfluid processing architecture pattern shown in FIG. 10(a), while the other had the pattern shown in FIG. 10(b). The tooling was produced by excimer laser ablation of a polyimide substrate to produce the desired pattern, and then electroplating the patterned areas to form a nickel tool with the indicated pattern. The tooling was then used in a continuous extrusion embossing process to produce articles as follows.

Polycarbonate pellets of Makrolon™ 2407 available from Mobay Corporation of Pittsburgh, Pa. were cast onto a heated microstructured nickel tooling surface containing ribs that were 50 micrometers tall and nominally 64 micrometers wide. These ribs corresponded to microchannels in the final molded article. The ribs were arranged in such a way that they connected several reservoirs that were 50 micrometers tall and 4 millimeters in diameter as depicted in FIGS. 10(a) and 10(b). The nickel tooling thickness was 508 micrometers and the tooling temperature was 210° C. Molten polycarbonate at a temperature of 282° C. was delivered to the nickel tooling in the form of a line of contact with the tool surface at a pressure of approximately $1.66 \times 10^7$ Pascals for 0.7 seconds to replicate the pattern on the tool surface. Coincident to forming the replicated pattern, additional polycarbonate was deposited on a continuous polymeric substrate located above the tooling having a thickness of approximately 103.9 micrometers. The combination of the tooling, the substrate, and molten polycarbonate was then cooled with air for 18 seconds to a temperature of approximately 48.9° C., thereby allowing the polycarbonate to solidify. The resulting molded product was then removed from the tool surface.

Example 2

The tooling used in Example 1 was heated to a temperature of 199–207° C. Poly(methylmethacrylate) pellets (Plexiglass™ DR 101 from Rohm and Haas Co. of Philadelphia, Pa.) were delivered, providing a line contact of polymer with the nickel tooling at a temperature of 271° C. and a pressure of $1.1 \times 10^7$ Pascals for 0.7 seconds. Coincident to forming the replicated pattern, additional poly (methylmethacrylate) was deposited on a continuous polymeric substrate located above the tooling having a thickness of approximately 212.1 micrometers. The combination of the tooling, the polymeric substrate, and the molten poly (methylmethacrylate) was then cooled with air for 18 seconds to a temperature of approximately 48.9° C., thereby allowing the poly(methylmethacrylate) to solidify. The resulting molded product was then removed from the tool surface.

Example 3

An ultraviolet radiation-curable blend of 59.5 parts by weight Photomer™ 316 (an epoxy diacrylate oligomer commercially available from Henkel Corp. of Ambler, Pa.). 39.5 parts by weight Photomer™ 4035 (2-phenoxyethyl acrylate monomer commercially available from Henkel Corp. of Ambler, Pa.), and 1 part Darocur™ 1173 photoinitiator (Ciba Additives, Tarrytown, N.Y.) was prepared. The blend was then laminated between the tool described in Example 1 that had been heated to 66° C. and a sheet of 0.5 mm thick polycarbonate (available from General Electric Corp. of Pittsfield, Mass. under the trade designation "Lexan"). The resin thickness was minimized using a hand-operated ink roller. The resulting structure was placed on a conveyor belt and passed at 7.6 meters per minute beneath a high intensity ultraviolet lamp ("D" lamp supplied by Fusion UV Systems, Inc. of Gaithersburg, Md.) operating at 600 watts/inch to cure the resin. The cured article, featuring a microfluid processing architecture-bearing polymer substrate integrally bonded to a polycarbonate substrate, was then removed from the tool.

Example 4

This example describes the preparation of a microfluidic device featuring a polymeric substrate bearing a plurality of microfluid processing architectures is combined with a polymeric substrate featuring microelectronic elements.

A polymer substrate 114, shown in FIG. 11(b), having multiple cross-dogbone microfluid processing architectures 116, was prepared by molding a poly(methylmethacrylate) film (DRG-100, Rohm and Haas) in a press using a nickel molding tool prepared following the general procedure set forth in Example 1. The tool measured 16.5 cm by 19 cm by 0.5 mm thick, and included five different cross-dogbone microfluid processing architectures 116, as shown in FIG. 11(a). The film and molding tool were brought into contact with each other at a temperature of 199° C. and a pressure of 3.5×10⁶ Pascals for 15 seconds, after which the pressure was increased to 6.2×10⁶ Pascals for a period of 10 minutes. Thereafter, the temperature was decreased to 74° C. while maintaining the pressure at 6.2×10⁶ Pascals for a period of 15 seconds. The resulting molded substrate 114 featured five different cross-dogbone microfluid processing architectures 116, each having a long channel measuring 28.5 mm long intersected by a short channel measuring 9 mm long. Each channel was terminated with fluid reservoirs measuring 5 mm in diameter. Both the channels and the reservoirs were 50 micrometers deep. The five architectures differed in the width of the channels, having widths of 64, 32, 16, 8, and 4 micrometers, respectively. One millimeter diameter inlet ports were then drilled through the center of each reservoir.

A flexible polymeric substrate 100, as shown in FIG. 11(b), bearing a plurality of microelectronic circuit elements, was prepared as follows. A polyimide sheet (available from DuPont under the designation "Kapton E") was vapor-coated with a tie-layer of chrome oxide which was then vapor-coated with a 2 micrometer layer of copper. A printed circuit board transfer resist (available from Techniks Inc., Ringoes, N.J., under the designation "Press-n-Peel") was then used to pattern microelectronic circuits on the copper-coated polyimide following the manufacturer's directions. The resulting substrate 100 contained six identical microelectronic circuit patterns, each having four electrically conductive copper traces 110. Each of the traces 110, in turn, terminated in a contact pad 112.

Following patterning, the exposed copper was removed using a copper etching bath. The chrome oxide tie-layer was then etched using a chrome oxide etchant and the transfer resist was removed using an acetone wash. The resulting copper traces were 500 micrometers wide with a 5 mm square contact pad at the peripheral tab.

Figure 12:
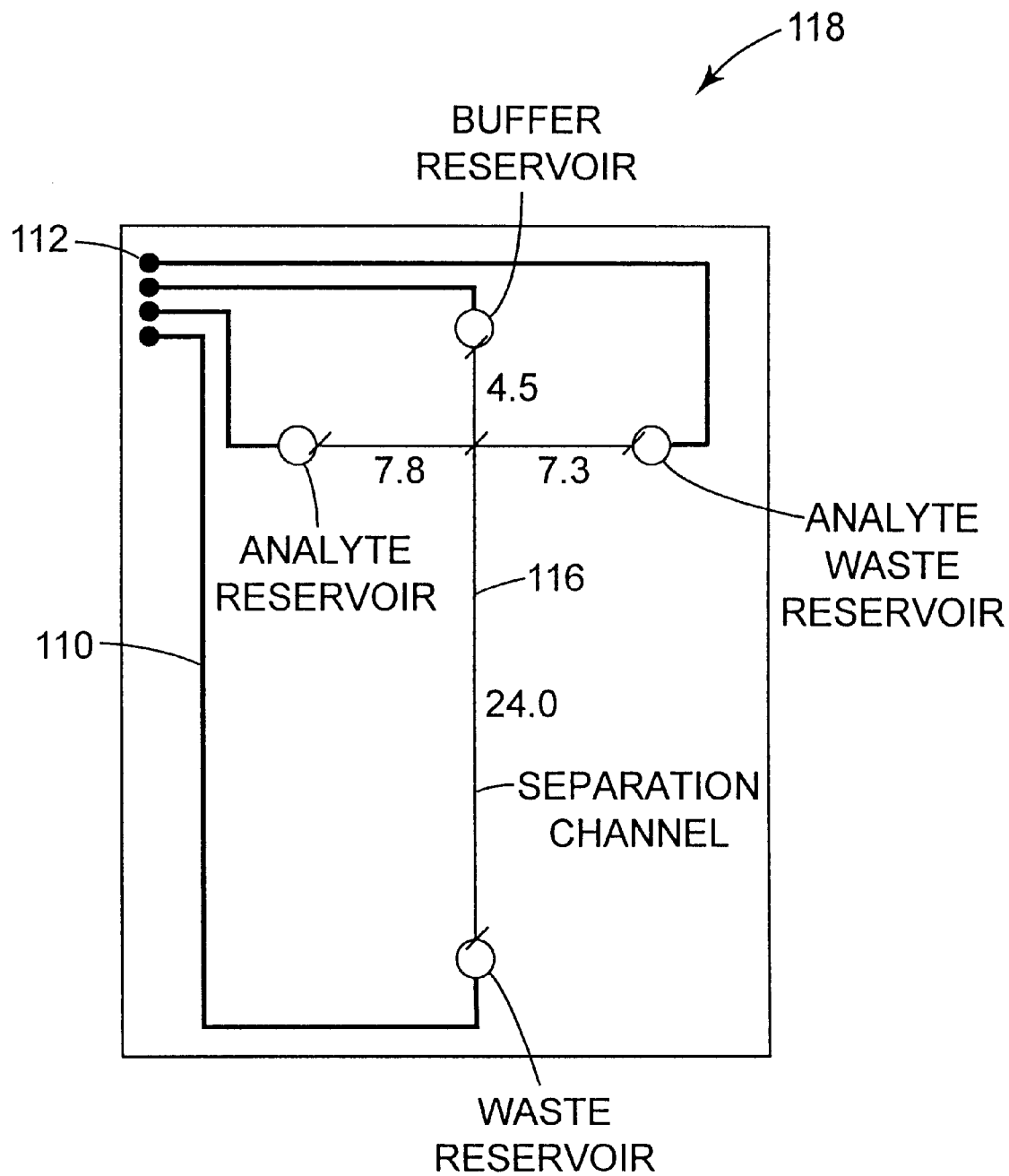
FIG. 12 is a top view of the substrate shown in FIG. 11(a) laminated in registration to the substrate shown in FIG. 11(b).

Substrate 100 was laminated to substrate 114 to create the microfluidic article 118 shown in FIG. 12 as follows. Substrate 100 and substrate 114 were both segmented to fabricate individual devices. A piece of double-sided adhesive tape (9443 tape available from 3M Company, St. Paul, Minn.) was patterned with holes to correspond to the fluid reservoirs in the cross-dogbone microfluid processing architecture 116. Each microfluid processing architecture 116 was then laminated to a circuit on substrate 100 such that the circuit-bearing face of substrate 100 mated with the microfluid processing architecture face of substrate 114, allowing contact between copper traces 1 10 and the fluid reservoirs of the microfluid processing architecture. Lamination was effected using a nip roller to provide line contact lamination of the two substrates. The resulting microfluidic article 118 was then used to demonstrate electrokinetic injections and electrophoretic separations as follows.

Microfluid processing architecture 116 was flooded with 4 mM $Na_2B_4O_7$ buffer (pH=9.0). The analyte reservoir was then filled with 20 micromolar fluorescein indicator dye dissolved in the same buffer. Voltages were applied to the four reservoirs by connecting contact pads 112 to a computer controlled voltage control circuit. Movement of the fluorescent indicator dye within the fluidic channels was monitored using a Leica DMRX epifluorescence microscope (Leica Inc., Deerfield, Ill.) equipped with a CCD camera (Panasonic CL 354, Panasonic Industrial Co., Secaucus, N.J.). For a pinched sample injection, voltages at the four reservoirs were set to provide voltage gradients from the analyte, sample, and waste reservoirs toward the analyte waste reservoir. This allowed for a good flow of fluorescein dye from the analyte reservoir through the injection tee and into the analyte waste reservoir. A slow flow of buffer from the separation channel and from the buffer reservoir created a trapezoidal plug of about 180 pL of fluorescein solution at the injection tee. Injection of this plug down the separation channel was effected by switching the voltages such that flow was predominantly from the buffer reservoir down the separation channel toward the waste reservoir. A tight bolus of fluorescein dye was observed to move down the separation channel.

The example was repeated using a mixture of fluorescein and calcein. In this case, injection of the mixed bolus down the separation channel resulted in rapid electrophoretic separation of the two materials.

Other embodiments are within the following claims.

What is claimed is:

1. A continuous process for preparing a molded article comprising:
   (a) providing a supply of flowable material and an open molding tool that comprises a molding surface;
   (b) continuously bringing the flowable material and the molding surface of the open molding tool into line contact with each other, forming a plurality of microfluid processing architecture patterns within said flowable material and thereafter solidifying the flowable material, thereby forming a molded article having at least one self-contained structure in accordance with each microfluid processing architecture pattern including at least one structural end point and at least one structural portion having a depth dimension of about 50 micrometers and a width dimension ranging from about 4 to about 64 micrometers; and (c) separating said molded article from said molding surface.

2. The process of claim 1, further comprising the step of attaching a substrate to said molded article to form a cover layer overlying the microfluidic processing architecture pattern and forming a fluid-tight seal with the microfluidic processing architecture.

3. The process of claim 1, further comprising introducing said molten material onto a surface of a substrate, and relatively moving said substrate and said open molding tool to bring said open molding tool and said molten material into line contact with each other.

4. The process of claim 3, wherein said substrate further comprises at least one of a microelectronic element, a microoptical element and a micromechanical element.

5. The process of claim 1, further comprising bonding a substrate comprising at least one of a microelectronic element, a microoptical element and a micromechanical element to said molded article.

6. The process of claim 2, wherein said substrate further comprises at least one of a microelectronic element, a microoptical element and a micromechanical element.

7. The process of claim 1, further comprising producing said molded article in the form of a roll including a plurality of microfluid processing architectures.

8. The process of claim 1, further comprising continuously bonding a substrate to said molded article.

9. The process of claim 8, wherein the substrate comprises at least one of a microelectronic, microoptical and a micromechanical element.

10. The process of claim 1, further comprising continuously bonding a substrate to said molded article to form a cover layer overlying said microfluid processing architectures.

11. The process of claim 10, wherein the substrate comprises at least one of a microelectronic, microoptical and a micromechanical element.

12. The process of claim 1, wherein said open molding tool comprises one of a roll and an endless belt.

13. The process of claim 2, wherein the step of attaching the substrate comprises laminating the substrate to said molded article.

14. The process of claim 13, wherein the step of laminating comprises line contact lamination of the molded article and the substrate.

15. The process of claim 2, wherein the step of attaching includes adhering said molded article to the substrate.

16. The process of claim 2, wherein the substrate comprises pressure sensitive tape including a pressure sensitive adhering surface.

17. The process of claim 2, wherein the step of attaching includes applying an adhesive between the molded article and the substrate to adhere the molded article to the substrate.

18. The process of claim 2, wherein the step of attaching occurs at about room temperature.

19. The process of claim 2, wherein the step of attaching comprises solvent welding of the substrate to the molded article.

* * * * *